United States Patent [19]
Lloyd et al.

[11] Patent Number: 5,915,386
[45] Date of Patent: Jun. 29, 1999

[54] METHOD AND DEVICE FOR DETECTING EDEMA

[75] Inventors: Lester John Lloyd, Orinda; Jorah Wyer, Mountain View, both of Calif.

[73] Assignee: Alere Medical Incorporated, San Francisco, Calif.

[21] Appl. No.: 08/959,242

[22] Filed: Oct. 28, 1997

[51] Int. Cl.[6] .................................................. A61B 19/00
[52] U.S. Cl. ......................................... 128/898; 128/897
[58] Field of Search .................................... 128/898, 897

[56] References Cited

U.S. PATENT DOCUMENTS

| | | | |
|---|---|---|---|
| 3,791,375 | 2/1974 | Pfeiffer ..................................... | 128/2 S |
| 3,890,958 | 6/1975 | Fister et al. ............................. | 128/2 S |
| 3,974,491 | 8/1976 | Sipe ....................................... | 340/272 |
| 4,144,749 | 3/1979 | Whitmore ................................ | 73/149 |
| 4,383,533 | 5/1983 | Bhagat et al. ........................... | 128/660 |
| 4,838,275 | 6/1989 | Lee ......................................... | 128/670 |
| 5,052,405 | 10/1991 | Batchelder ............................. | 128/774 |
| 5,323,650 | 6/1994 | Fullen et al. ............................ | 73/172 |
| 5,385,069 | 1/1995 | Johnson, Jr. ............................ | 73/571 |

OTHER PUBLICATIONS

Breytenbach, H.S., "Objective Measurement of Post–Operative Swelling," *Int. J. Oral Surg.* (1978) vol. 7;386–392.

Dramaix, M. et al., "Serum Albumin Concentration, Arm Circumference, and Oedema and Subsequent Risk Of Dying In Children In Central Africa," *BMJ* (1993) vol. 307:710–713.

Kushner, Robert F., et al., "Estimation of Total Body water By Bioelectrical Impedance Analysis[1–3]," *The American journal of Clinical Nutrition* (1986) vol. 44:417–424.

Lindahl, O.A., et al., "Impression Technique for the Assessment of Oedema: Comparison With A New Tactile Sensor That Measures Physical Properties Of Tissues," *Med. & Biol. Eng. & Comput.,* (1995) vol. 33:27–32.

Miyazaki, S., et al., "Foot–Force Measuring Device For Clinical Assessment of Pathological Gait," *Med. & Biol. Eng. & Comput.* (1978) vol. 16:429–436.

Mridha, M. et al., "Fluid Translocation Measurement," *Scand j Rehab Med* (1989) vol. 21:63–69.

Mridha, M., et al., "Noninvasive Method For The Assessment of Subcutaneous Oedema," *Medical & Biological Engineering & Computing* (1986) vol. 24:393–398.

Davies, G. et al., "An Automatic Device For The Measurement of Oedema In The Feet Of Rats and Guinea Pigs," *Med. & Biol. Enging.* (1971) vol. 9:567–570.

Starr, Thomas W., "A Computerized Device for the Volumetric Analysis of the Residual Limbs of Amputess," *Bullletin of Prosthetics Research BPR 10–33* (1980) vol. 17, No. 1,:98–102.

Swedborg, Iwona, "Voluminmetric Estimation of the Degree of Lymphedema and its Therapy By Pneumatic Compression," *Scand J Rehab Med* (1977) vol. 9:131–135.

*Primary Examiner*—Mickey Yu
*Assistant Examiner*—Dinh X. Nguyen
*Attorney, Agent, or Firm*—Bozicevic, Field & Francis LLP; Bret Field

[57] ABSTRACT

Methods and devices are provided for detecting the presence of edema in a mammalian host. In the subject methods, a cross-sectional dimension of at least one limbic extremity, preferably a lower limbic extremity such as an ankle or foot, is measured to obtain a measured value. The measured value is then compared to a control value and any difference is identified. The difference is then related to the presence of edema in the patient. The subject methods find use in the diagnosis and management of diseases characterized by the presence of edema as a physical manifestation, particularly congestive heart failure.

22 Claims, 2 Drawing Sheets

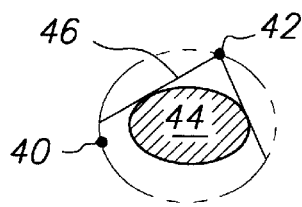
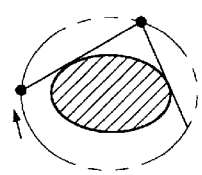
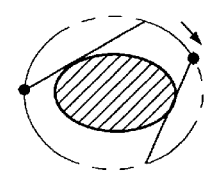
FIG. 4A  FIG. 4B  FIG. 4C
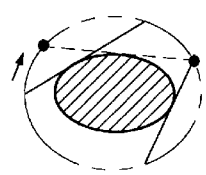
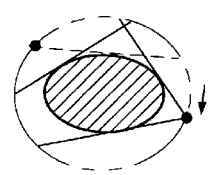
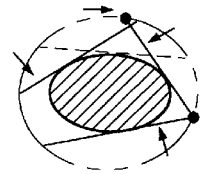
FIG. 4D  FIG. 4E  FIG. 4F
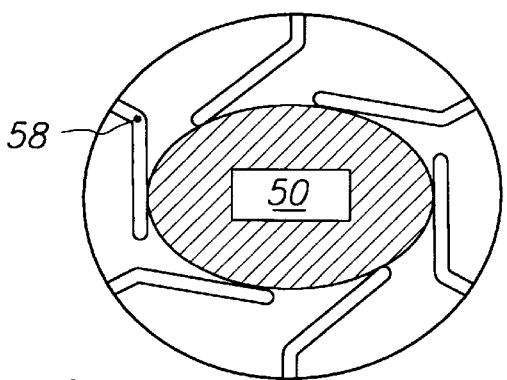
FIG. 5
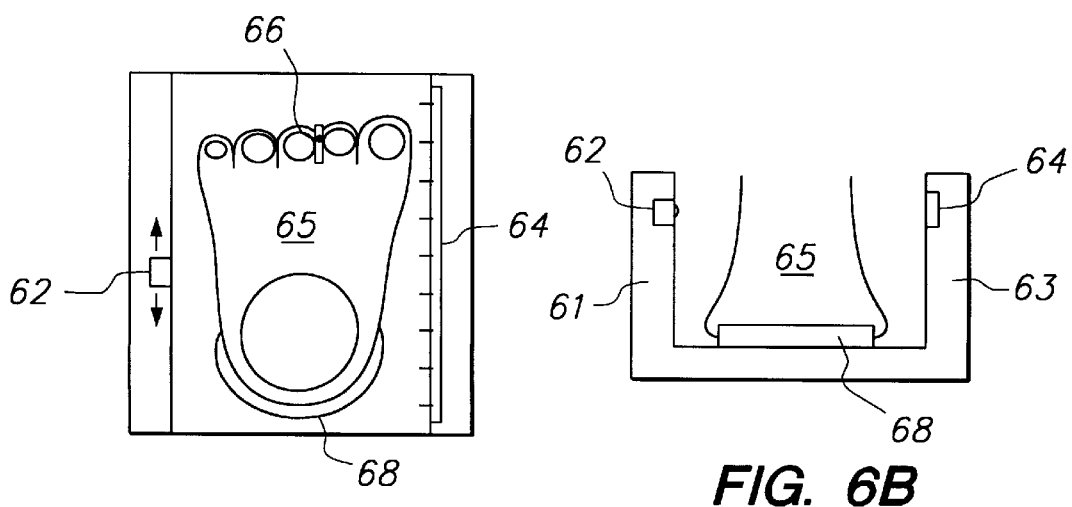
FIG. 6A  FIG. 6B

METHOD AND DEVICE FOR DETECTING EDEMA

TECHNICAL FIELD

The field of this invention is diseases characterized by edema.

BACKGROUND OF THE INVENTION

Edema is defined as the abnormal accumulation of fluid in connective tissue. Edema typically results from a combination of passive venous congestion and salt and water retention, and may be systemic or localized to a particular region of the body. Dependent edema, in which fluid accumulates in the tissues of the limbic extremities, e.g. ankle, foot and the like, is a physical manifestation of a number of different human disease conditions. Dependent edema first appears in the feet and ankles of the ambulatory patient, and in the posterior surface of the calves and skin overlying the sacrum in the bedridden patient. Disease conditions characterized by the presence of dependent edema include local venous or lymphatic obstruction, cirrhosis, hypoalbumenia, and congestive heart failure.

In congestive heart failure, the presence of edema in the lower extremities is a valuable diagnostic marker for the presence of the disease. In addition to serving as a marker for the presence of congestive heart failure, the progression of the edemic state can be monitored over time and the progression of the edemic state related to the progression of the disease.

One way of detecting the presence of edema is to determine fluid volume change of the patient. A number of different technologies have been developed to identify the volume change, and include those based on the use of water or air-filled cuffs, mercury strain gauge, fiber optic strain gauge, and airborne ultrasound. Such technologies have principally been employed to measure venous blood flow and to sense the volume pulsations created by the heart.

Another method for detecting the presence of edema in a patient is the "pitting" method. In this method, a physician's thumb or finger is pressed into the patient's skin next to a bony surface (e.g., tibia, fibula, or sacrum). When the physician's finger is withdrawn, an indentation persists for a short time. The depth of the "pit" is estimated and generally recorded in millimeters, although subjective grading systems (e.g. "+++", etc.) have also been described. In general, the distribution of edema is also noted, as the amount of fluid is roughly proportional to the extent and the thickness of the pit.

Because dependent edema is a physical manifestation of a number of different disease conditions, the development of accurate methods for the detection of edema is of interest. Of particular interest is the development of methods which are sufficiently inexpensive and simple so as to be amenable to use in both conventional and out-patient health-care settings.

Relevant Literature

Scientific American Medicine (Dale & Freeman eds)1:II provides a review of congestive heart failure, physical manifestations and methods for the treatment thereof.

Lindahl & Omata, Med. Biol. Eng. Comput. (1995) 33:27-32 provide a description of methods of assessing edema.

Other references of note include U.S. Pat. Nos.: 3,791,375; 3,890,958; 3,974,491; 4,144,749; 4,383,533; 5,052,405; 5,323,650; and 5,385,069; as well as Swedborg, Scand. J. Rehab. Med. (1977) 9:131-135; Mridha & Ödman, Scand. J. Rehab. Med. (1989)21:63-39; Mridha & Ödman, Med. Biol. Eng. Comput. (1986) 24:393-398; Kushner et al., Am. J. Clin. Nut. (1986) 44:417-424; Breytenbach, Int. J. Oral Surg. (1978) 7:386-392; Davies et al., Med. Biol. Eng. Comput. (1971) 9:567-570; Lindhal et al., Med. Biol. Eng. Comput. (1991) 29:591-597; Iwakura, Med. Biol. Eng. Comput. (1978) 16:429-436; and Starr, BPR (1980) 17:98-102.

SUMMARY OF THE INVENTION

Methods and devices are provided for detecting and/or monitoring edema. In the subject methods, a cross-sectional dimension of at least one limbic extremity, preferably an ankle or foot, of a mammalian host, is accurately measured. Of particular interest is the measurement of the diameter or cross-sectional area as the cross-sectional dimension. The measured value is then related to the presence or absence of edema. In the subject methods, the cross-sectional dimension may be measured a plurality of times, usually according to a predetermined schedule, so that the progression of the edemic state may be monitored. The subject methods find use in the diagnosis and management of diseases characterized by the presence of edema.

BRIEF DESCRIPTION OF THE FIGURES

FIGS. 4a to 4f depict a device for measuring a cross-sectional area according to the subject invention.

FIG. 5 depicts a device for measuring a cross-sectional area according to the subject invention. FIGS. 6A & 6B depict a device for measuring a cross-sectional dimension according to the subject invention.

DESCRIPTION OF THE SPECIFIC EMBODIMENTS

Figure 1A:
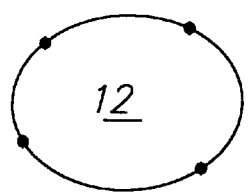
FIGS. 1a & 1b depict show four non points of a non-circular limb and the four circles that can be derived thereof.

Methods and devices are provided for detecting the presence of and/or monitoring edema. In the subject methods, a cross-sectional dimension of at least one limbic extremity, preferably an ankle or foot, of a mammalian host, is accurately measured. Of particular interest are methods in which the cross-sectional dimension is either the diameter or the cross-sectional area of the extremity. The measured value is then related to the presence or absence of edema. In the subject methods, the cross-sectional dimension may be measured a plurality of times, usually according to a predetermined schedule, so that the progression of the edemic state may be monitored. The subject methods find use in the diagnosis and management of diseases characterized by the presence of edema, particularly congestive heart failure.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The first step of the subject methods is to measure a cross-sectional dimension of a limbic extremity of the mammalian host, e.g. human patient. Generally the limb that is measured is a lower extremity or region, portion or location thereof, where usually the cross-sectional dimension of at least one of the ankle and foot are measured. In the subject methods, the cross-sectional dimension of only a single region, portion or location of the limb may be measured, or the cross-sectional dimension of a plurality of locations may be measured, where when a plurality of locations are measured, usually the number of different locations that are measured will not exceed three, and more usually will not exceed two.

The cross-sectional dimension that is measured may be the diameter, radius or cross-sectional area of the extremity at a selected location, where preferred cross-sectional dimensions are the diameter and the cross-sectional area.

For measuring the cross-sectional dimension, a measuring device that is capable of providing at least an approximation or measurement of the limb cross-sectional dimension is employed. Preferably the device is simple, inexpensive, and able to provide data that can readily be input into a microprocessor. The nature of the device used to measure the cross-sectional dimension will necessarily depend on the particular cross-sectional dimension to be measured.

Where the cross-sectional dimension to be measured is the diameter of the extremity at a particular location, one may use a device comprising a light detector and light source as depicted in FIG. 6A and 6B. As shown in FIG. 6A and 6B, the device consists of two towers 61 & 63 one of which has a movable photodetector 62 and the other of which has a light source 64 running the length of the device. The light and detector will be configured such that the detector detects only light that is perpendicular to it. As such, a light columnator will be employed, where the columnating means may be part of the detector and or the source. For example, the columnator could be an extended thin tube attached to the source or the detector. Alternatively, the light source could be a point source that moves with the detector such that when the limb is between the source and detector, the detector detects no light from the source. In using the device to determine the diameter of an extremity, the extremity (e.g. a foot, as shown in the FIGS. 6A & 6B) is placed between the light detector and the light source. The moving detector is then moved back and forth along the length of the extremity at the location of interest for which a diameter measurement is desired and points of transition between light and dark are recorded. From the recorded data, the diameter of the extremity is determined. To ensure that an accurate measurement is obtained each time, the device may further comprise a reference means for ensuring that the extremity is placed between the light source and the detector at the same location each time a measurement is taken. For example, where the extremity is a foot 65, the device may further comprise a heal counter 68 and a toe alignment means 66 as shown in FIG. 6A and 6B.

Where the cross-sectional dimension is the area of the extremity, a variety of different methods of determining the cross-sectional area of the extremity may be employed. One method of determining the cross-sectional area of the limb is to impose at least three distinct, non-parallel tangent lines on the periphery of the limb. In this method, at least three tangent lines will be imposed, where the number of tangent lines may be much higher, as discussed below. From the tangent lines, a series of circles is derived (the number of circles that can be derived equals $n!/(3!*(n-3)!)$ or $^nC_3$ where n is the number of lines or points, e.g. for 1 line, 0 circles; for 2 lines, 0 circles; for 3 lines, 1 circle; for 4 lines, 4 circles; for 5 lines, 10 circles . . . ). The areas of these circles is then compared, e.g. averaged or otherwise compared, to arrive at value that approximates the cross-sectional area of the extremity.

A device for measuring the circumference of an extremity through the production of at least three tangent lines, as described above, is depicted in FIGS. 4a to 4f. The device has a light 40 and a detector 42 both of which are capable of independently moving around the periphery of the extremity 44 at roughly the same vertical height. In using this device to produce at least the three requisite tangent lines, the extremity will first be introduced and the light and detector positioned relative to one another such that the detector is in the shadow of the extremity see FIG. 4A. The detector is then moved around the circumference of the extremity, while maintaining the light source in a constant position, until the detector emerges from the shadow of the extremity and registers light from the light source. The absolute position of both the detector and the light source are then recorded. The light source is then moved along the circumference, while maintaining the position of the detector, until the detector is again in the shadow of the extremity. The detector is then moved while maintaining the position of the light source until the detector again registers light from the light source. The absolute positions of the light source and detector are again recorded. In this manner, a series of at least three tangent lines is produced at different positions of the periphery of the extremity see FIGS. 4B to 4F. The produced tangent lines are then use to determine the periphery of the extremity.

Alternatively, the device depicted in FIG. 5 can be used to impose the series of tangent lines from which the cross-sectional area is derived, as described above. In FIG. 5, the surface of the extremity 50 is contacted at a plurality of distinct locations on the periphery with a plurality of positional sensors 58. By plurality of positional sensors is meant at least 3, usually at least 4 and more usually at least 5, where the number of different positional sensors may be as high as 8 or more, but will usually not exceed 7 and more usually will not exceed 6. The sensors are used to determine the angle at which the member contacts the limb and thus the equation of the line represented by the member. The sensors may be any convenient sensors capable of providing positional information or data to a processing means which in turn is capable of deriving the circumference of the extremity from the positional information or data. Representative sensing means include: piezo-films, strain-gages, angular potentiometers, encoders, and the like. The sensors may be positioned on an extender means, as shown in FIG. 5, where the extender means may be fabricated from compliant material such that the extremity can easily be positioned, or be fabricated from a more rigid material, in which case the device will provide for the extenders to be retracted from the extremity surface upon introduction and removal of the extremity.

Figure 1B:
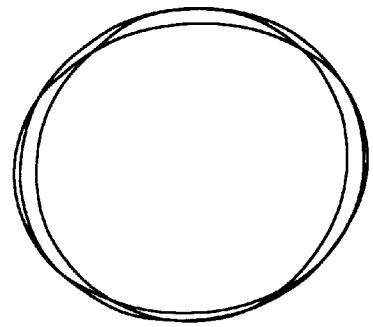

Instead of using a series of tangent lines to obtain the cross-sectional area of the limb, a series of at least three distinct points falling on the periphery of the extremity can be employed. FIG. 1a shows a limb having four points selected on the periphery thereof. From the four points, a series of four circles can be derived. FIG. 1b. The areas are then averaged to obtain the cross-sectional area of the limb.

Figure 2:
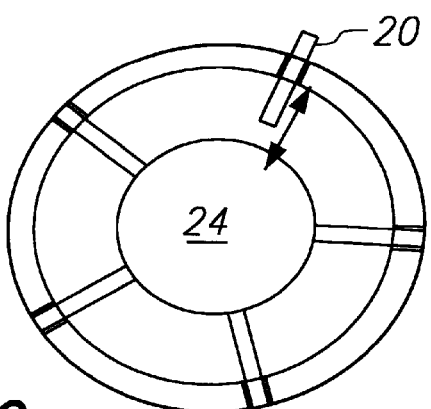
FIG. 2 shows a device according to the subject invention that can be used to measure the cross-sectional area of a limb.
Figure 3A:
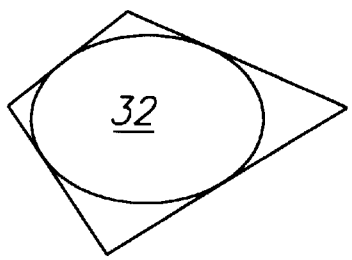
FIG. 3A and 3B shows how four lines can enclose a non-circular limb and the four circles that can be derived therefrom.
Figure 3B:
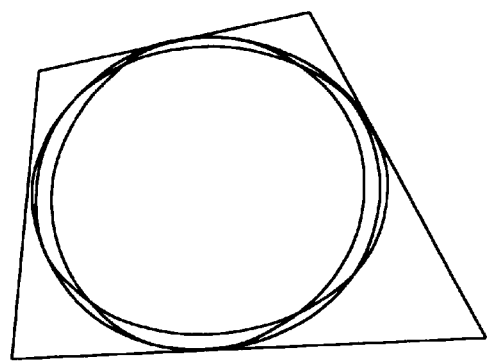

A device for determining the cross-sectional area using at least three distinct points is depicted in FIG. 2. In the device of FIG. 2, a plurality of linear actuators 20 are positioned around the periphery of the limb 28 and are capable of moving radially inward or outward from the limb. Positioned at the end of each actuator is a micro switch or contact sensor. The position of the actuator end is determined by the position of the actuator bushing and the distance the actuator is protruding. Encoders, linear potentiometers or other methods can determine this distance.

In other embodiments, other higher order analytical shapes, e.g. ellipses or other conical shapes, are derived from the points or tangent lines and used to derive the cross sectional area of the limb.

In the subject methods, the next step is to compare the measured cross-sectional dimension value to a control value. The control value will be a value which corresponds to the cross-sectional dimension of the limb at the location that is measured in the absence of the edemic state. Where possible to measure the limb in the absence of edema, such as in the case of pregnancy when the measurement can be made at an early time in anticipation of later indications of edema or prior to a surgical operation likely to result in edema, then such non-edemic measurements can be used as a control value. Most often this is not possible as the desirability of edemic measurements is not apparent until the edema is already a problem. In this case the best indication of the non-edemic control value is simply the lowest value obtained from a series of measurements taken over a period of time. If a microprocessor or other computer device is available, then the recording and displaying of the measurements allows an instant graphic display of not only the measured amount of edema but, often more importantly, whether the condition is worsening or improving. The measured cross-sectional value and the control value will be compared and any difference will be identified.

The presence of a positive difference between the measured value and the control value is then correlated to the presence of swelling in the region of measurement and edema in the patient. Conversely, the absence of a difference or a negative difference may be related to the absence of the edemic state. Accordingly, the final step of the subject methods is to attribute the presence of a positive difference to the presence of edema in the patient.

The subject methods may be used to make multiple measurements over a given period of time so that the progression of the edemic state may be monitored. Where multiple measurements are made, the measurements will typically be made according to a schedule, where the measurements may be made hourly, daily, weekly, monthly and the like.

A microprocessor may be used in the conjunction with the subject methods. For example, the measured value may be input into a microprocessor device that then takes the data and performs the comparison with a predetermined control value and provides a readout of any difference. The microprocessor could also transmit the input data to a remote site for further processing and use. Such an embodiment finds use in applications where measurements are taken at sites remote to the medical personnel in charge of interpreting the results, such as in outpatient clinics, at the home and the like.

The subject methods find use with a variety of mammalian hosts where the detection of dependent edema is desired. Mammalian hosts with which the subject methods may find use include highly valuable, rare and exotic animals, domestic animals, such as livestock and pets, and humans.

Of particular interest is the use of the subject methods in the diagnosis and management of human diseases in which dependent edema is a physical manifestation, such as venous or lymphatic blockage, cirrhosis, hyperalbumenia and congestive heart failure, where congestive heart failure is of particular interest.

In using the subject methods in the diagnosis of congestive heart failure, the detection of edema by the subject methods is used as an indication of the presence of congestive heart failure. In making such diagnoses, jugular venous distention may also be detected, since the presence of both conditions can be used as assurance that the underlying disease condition is congestive heart failure, and not another disease characterized by the presence of dependent edema, such as local venous or lymphatic obstruction, cirrhosis or hypoalbumenia.

Also of particular interest is the use of the subject methods in the management of congestive heart failure. In managing congestive heart failure, a plurality of measurements will be taken according to a schedule and the progression the edemic state will be monitored. In this manner, the affect of various treatment methodologies on the symptoms associated with and/or the progression of the underlying disease can be assessed.

The following examples are offered by way of illustration and not by way of limitation.

EXPERIMENTAL

A. A sixty one year old man with congestive heart failure resides at home with a care giver. A computerized telephonic monitoring system is installed which transmits information to a centralized nursing station. The system requires the patient to complete a daily monitoring cycle which includes answering questions on his general health, sleeping, appetite, and any unusual symptoms. As well, the patient stands places his foot on an indicated location on a flat plate attached between a light source and detector, as shown in FIGS. 6A to 6B. The diameter of the foot is determined and, at a later time, the computer system transmits the entire information set collected, including the edema measurements, to the central station. With an analysis of this daily information, a physician has early warning information, and can provide prompt care, avoiding acute episodes. Of particular interest is use of the subject methods and devices as part of the patient interface system disclosed in U.S. patent application Ser. No. 08/958,689 (atty docket no. ALE-1P) entitled Patient Interface System and filed concurrently herewith, the disclosure of which is herein incorporated by reference.

It is evident from the above results and discussion that improved methods for detecting dependent edema in a mammalian host are provided. Because the subject methods use relatively simple and inexpensive measurement devices, they are amenable for use in high volume situations and out patient settings by moderately skilled personnel, and therefore provide an attractive alternative to currently employed methods of detecting edema which are based on the detection of volume changes.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting the presence of edema in a mammalian host, said method comprising:

optically measuring a cross-sectional dimension value of at least one limbic extremity of said host; and relating said value to the presence of edema in said host;

whereby the presence of edema in said host is detected.

2. The method according to claim 1, wherein said extremity is a lower extremity.

3. The method according to claim 2, wherein said lower extremity is selected from the group consisting of ankle and foot.

4. The method according to claim 1, wherein said relating step comprises comparing the measured cross-sectional dimension value to a control value and attributing any difference in values to the presence or absence of edema.

5. The method according to claim 1, wherein said cross-sectional dimension is the diameter of the extremity.

6. The method according to claim 1, wherein said cross-sectional dimension is a cross-sectional area of the extremity.

7. A method for detecting the presence of edema in a human, said method comprising:

measuring a cross-sectional area of at least one lower extremity in said host by; (a) imposing at least three distinct, non-parallel tangent lines on the periphery of said extremity; (b) deriving a series of circles from said tangent lines; (c) determining the areas of said circles, whereby said cross-sectional area is measured;

comparing the measured cross-sectional area to a control value to obtain a difference; and attributing any difference to the presence or absence of edema in said human;

whereby the presence of edema in said human is detected.

8. The method according to claim 7, wherein said lower extremity is selected from the group consisting of foot and ankle.

9. The method according to claim 7, wherein said measured cross-sectional area is input into a microprocessor.

10. The method according to claim 7, wherein said measured cross-sectional area is transmitted to a site remote from the site where said cross-sectional dimension is measured.

11. The method according to claim 7, wherein said cross-sectional area is measured a plurality of times and the progression of said edema is monitored.

12. The method according to claim 11, wherein said human suffers from congestive heart failure.

13. The method according to claim 11, wherein said detection of edema is used in at least one of the diagnosis and management of said congestive heart failure.

14. A method for detecting the presence of edema in a patient suffering from congestive heart failure, said method comprising;

optically measuring a cross-sectional dimension value of at least one lower extremity of said patient, wherein said cross-sectional dimension value is selected from the group consisting of a diameter and a cross-sectional area and said lower extremity is selected from the group consisting of foot and ankle;

comparing the measured cross-sectional dimension value of said lower extremity to a control value and determining any difference; and attributing said difference to the presence or absence of edema in said patient;

whereby the presence of edema in said patient is detected.

15. The method according to claim 14, wherein said method is used in the diagnosis of said congestive heart failure.

16. The method according to claim 14, wherein said method is used in the management of said congestive heart failure.

17. The method according to claim 16, wherein said measuring is repeated a plurality of times and the progression of said edema, is monitored.

18. The method according to claim 14, wherein said measured cross-sectional dimension is input into a microprocessor.

19. The method according to claim 14, wherein said measured cross-sectional dimension value is transmitted to a remote site.

20. The method according to claim 17, wherein said repeated measurements are taken according to a schedule.

21. A method for detecting the presence of edema in a human, said method comprising:

measuring a cross-sectional area of at least one lower extremity in said host by: (a) imposing at least three distinct points on the periphery of said extremity; (b) deriving a series of circles from said points; and (c) determining the areas of said circles, whereby said cross-sectional area is measured;

comparing the measured cross-sectional area to a control value to obtain a difference; and attributing any difference to the presence or absence of edema in said human;

whereby the presence of edema in said human is detected.

22. The method according to claim 21, wherein said lower extremity is selected from the group consisting of foot and ankle.

* * * * *